United States Patent [19]

Smith

[11] Patent Number: 4,568,676
[45] Date of Patent: Feb. 4, 1986

[54] METHOD OF INHIBITING AGGREGATION USING THROMBOXANE SYNTHETASE INHIBITOR IN COMBINATION WITH A CYCLIC AMP PHOSPHODIESTERASE INHIBITOR

[75] Inventor: J. Bryan Smith, Philadelphia, Pa.

[73] Assignee: Thomas Jefferson University, Philadelphia, Pa.

[21] Appl. No.: 640,021

[22] Filed: Aug. 10, 1984

Related U.S. Application Data

[63] Continuation of Ser. No. 555,289, Nov. 25, 1983, abandoned, which is a continuation of Ser. No. 341,082, Jan. 20, 1982, abandoned.

[51] Int. Cl.$^4$ ............... A61K 31/52; A61K 31/505; A61K 31/535
[52] U.S. Cl. .................................. 514/258; 514/227; 514/259; 514/264; 514/267; 514/277; 514/307; 514/343; 514/356; 514/396; 514/399
[58] Field of Search ............... 424/251, 253, 258, 263, 424/273 R; 514/227, 258, 259, 264, 267, 277, 307, 343, 356, 396, 399

[56] References Cited

PUBLICATIONS

Chemical Abstracts, 89:123338m (1978) [Gorman, R., et al., Adv. Cyclic Nucleotide Res., 1978, 9, 597–609].
Chemical Abstracts, 81:33946p (1974) [Hugues, J., Acta Univ. Carol., Med., Monogr., 1972, 53/54, 179–184].
Rybicki, J., et al., Thrombosis Research, 30, 407–414 (1983).
Haslam, R., et al., Journal of Biochemistry, 176:83–95 (1978).
Lefkowitz, R., et al., TIPS, pp. 314–318 (Jul., 1980).
Smith, S., et al., Journal of Biological Chemistry, 257:10471 (1982).
Smith, J., Thrombosis Research, 28:477–485, 1982.
Macintyre, D., Platelets in Biology and Pathology-2, Chapter 9, Elsevier, New York, 1981, pp. 234–240.
Watanabe, T., et al., Journal of Biological Chemistry, vol. 257, pp. 14847–14853, 1982.
Rittenhouse, S., et al., Am. Soc. for Clin. Inves., 70:1216, 1982.
Hampton, J., et al., Cardiovascular Research, 1:101–107, (1967).
Mustard, J., et al., Biochemical Pharmacology, 22:3151–3156, (1972).
Kloeze, J., Biochim. Biophys. Acta, 187:185–292 (1969).
Smith, J., et al., Thrombosis Research, 5:291–299, (1974).
Johnson, R. A., et al, Prostaglandins, vol. 12, No. 6, pp. 915–928 (1976).
Gryglewski, R. J., et al., Thrombosis Research, vol. 13, No. 2, pp. 153–165 (1978).
Gorman, R. R., et al., Prostaglandins, vol. 13, No. 3, pp. 377–388 (3/1977).
Vigdahl, R. L., et al., Thrombosis Research, 21:547–555, (1981).
Fleming, J. S., et al., Thrombosis Research, 15: 373–388 (1979).
Ardlie, N. G., et al., Thromb. Diath. Haemorrh., 18:670–673, (1967).
Goodman et al, The Pharmacological Basis of Therapeutics, 6th Ed., Macmillian Pub. Co., New York, pp. 830 and 592–607 (1980).

(List continued on next page.)

Primary Examiner—Richard A. Schwartz
Attorney, Agent, or Firm—Woodcock Washburn Kurtz Mackiewicz & Norris

[57] ABSTRACT

A novel method of inhibiting blood platelet aggregation is disclosed which comprises the use of a CAMP inhibitor together with an inhibitor of thromboxane synthesis. While inhibitors of thromboxane synthesis are only weak inhibitors of platelet aggregation, the addition of only a small amount of a CAMP inhibitor has been found to result in a synergistic increase in the degree of platelet aggregation resulting from such combined additions. Marked increases over the otherwise expected culumative effects of these inhibitors have been demonstrated using combination of various thromboxane synthetase inhibitors and various CAMP inhibitors.

15 Claims, 5 Drawing Figures

PUBLICATIONS

Oelz, O., et al., *Prostaglandins,* vol. 13, No. 2, pp. 225–234 (Feb., 1977).

Hamberg, M., et al., *Proc. Nat. Acad. Sci., USA,* 71:3400–3404, (Sep., 1974).

Ellis, E., et al., *Science,* 193:1135–1137 (1976).

Needleman, P., et al., *Proc. Natl. Acad. Sci, USA,* vol. 74, No. 4, pp. 1716–1720 (1977).

Tyler, H. M., et al., *The Lancet,* pp. 629–632, (Mar. 21, 1981).

Taniguchi, K., et al., Int. Prostaglandin Conference, Washington, D.C., p. 82, 5/79.

Tai, C., et al., Int. Prostaglandin Conference, Washington, D.C., p. 115, 5/79.

Hampton, T., et al., *Cardiovasc. Res.,* 1967, 1, 101–107.

METHOD OF INHIBITING AGGREGATION USING THROMBOXANE SYNTHETASE INHIBITOR IN COMBINATION WITH A CYCLIC AMP PHOSPHODIESTERASE INHIBITOR

BACKGROUND OF THE INVENTION

This is a continuation of application Ser. No. 555,289, filed Nov. 25, 1983, now abandoned, which in turn is a continuation of Ser. No. 341,082, filed on Jan. 20, 1982, now abandoned.

The present invention relates to a novel and useful method for inhibiting blood platelet aggregation.

Blood platelets, sometimes referred to as thrombocytes, are small cells which exist in large numbers in blood and form a vital part of the normal hemostatic mechanism. When blood vessels are injured and bleeding occurs, platelets adhere to the subendothelial collagen in the damaged vessel wall and then aggregate to form a platelet plug which arrests the bleeding. This platelet plug is then consolidated by the formation of a fibrin network which results from activation of the blood clotting system. The pathological extension of the hemostatic platelet plug is called a thrombus. This may occur in vessels where the inner wall is injured and bleeding does not occur as, for example, in atherosclerosis. Thrombus formation may block the flow of blood to a major organ either directly or because emboli (consisting of platelet aggregates) break off from the thrombus, travel downstream in the blood and lodge in small blood vessels to completely occlude them. Regardless of the mechanism it is generally conceded that thrombosis plays a critical role in stroke, pulmonary embolism and myocardial infarction. It also is generally believed that if the tendency toward undesired platelet aggregation could be reduced, the incidence of thrombotic episodes would be reduced (For more detailed review see Mustard and Packham, *Biochemical Pharmacol.* 22 pp. 3151–3156, 1973.

Certain prostaglandins including 11α,15(S)-dihydroxy-9-oxo-13-transprostenoic acid (PGE$_1$), 9α,15(S)-dihydroxy-11-oxo-5-cis-13-trans-prostadienoic acid (PGD$_2$) and 9-deoxy-6, 9α-epoxy-11,α15(S)-dihydroxy-5-cis-13-trans-prostdienoic acid (PGI$_2$, prostacyclin) have been demonstrated to inhibit platelet aggregation Kloeze, *Biochem. Biophys. Acta.* 187 pp. 285–292, 1969; Smith et al *Thromb. Res.* 5, pp. 291–299, 1974; Johnson et al *Prostaglandins* 12, pp. 915–926, 1976. However, while the above disclosed prostaglandins are known to possess platelet antiaggregating properties, their use for preventing thrombosis is seriously limited because their antiaggregating properties are rapidly destroyed in the circulation. The anti-platelet effect achieved when these prostaglandins are infused into the circulation is lost within a few minutes after the infusion is stopped. See Gryglewski, *Thromb. Res.* 13, 153–163, 1978. Moreover, adverse side-effects such as sudden weakness, nausea, pallor, fall in heart rate and in blood pressure are associated with prostaglandin infusions.

There is little doubt that prostaglandins inhibit aggregation as a result of the stimulation of adenylate cyclase and the consequent accumulation of cyclic AMP in platelets. Gorman et al, *Prostaglandins* 13, pp. 378–388, 1977. Certain other drugs inhibit platelet aggregation because they increase cyclic AMP by inhibiting phosphodiesterase ("CAMP inhibitors"), the enzyme that hydrolyses cyclic AMP in platelets. The most potent of these drugs presently known are quinazolinone derivatives such as BL-3459; Vigdahl and Ferber, *Throm. Res.* 21, pp. 547–557, 1981; and BL-4162A, anagrelide: Fleming and Buyniski, *Thromb. Res.* 15, pp. 372–388, 1979. Classes of drugs with similar properties include papaverine, Hampton et al., *Cardiovas. Res. Center Bull* (Baylor Univ. Houston)1, pp.101–107, 1967; Pyrimidopyrimidines such as RA233 and RA8 (dipyridamole): Emmons et al, *Brit. Med. J.* 2, pp. 468–427, 1967 and methylxanthines such as isobutyl methylxanthine and theophylline, Ardlie et al, *Thromb. Diath. Haemorrh,* 18, pp. 670–673, 1967. There is evidence in animal models that these types of drugs have antithrombotic activity when given orally. However, there biochemical effects are most certainly not confined to the platelet when the drug is circulating in vivo. For example, papaverine's reported side effects include hepatic toxicity, facial flushing, tachacardia, drowsiness, and gastrointestinal upset. Papaverine and dipyridamole are also nonspecific smooth muscle relaxants and vasodilators. These drugs have not been demonstrated to be of therapeutic value in any condition. Goodman and Gilman, Macmillan Publishing Co. N.Y., Sixth Edition, p. 830, 1980. Methyl xanthines also relax smooth muscle and have numerous other properties. Goodman and Gilman, Sixth Edition, pp. 592–607.

A third new class of compounds presently being considered for use as antithrombotic agents are inhibitors of thromboxane synthesis. Smith et al., in *J. Clin. Invest.* 52, pp. 965–969 (1973) demonstrated that prostaglandins PGE$_2$ and PGF$_2$ α are formed and released during platelet aggregation in response to collagen, epinephrine and adenosine diphosphate (ADP). Olez et al. in *Prostaglandins* 13, pp. 225–234 (1977) demonstrated that there is also formation of the potent inhibitor of aggregation PGD$_2$, disclosed above. However, Hamberg et al. in *Proc. Natl. Acad. Sci.* USA 71, 3400–3408, 1974 revealed that platelets make only small amounts of PGE$_2$, PGF$_2$α and PGD$_2$ but that, via a common intermediate the prostaglandin endoperoxide PGH$_2$, the platelets produce relatively large amounts of compounds later named thromboxanes, Hamberg et al., *Proc. Natl. Acad. Sci.* USA 72, pp. 2994–2998, 1975. Thromboxane A$_2$ (TxA$_2$) is a potent vasoconstrictor of rabbit aorta and coronary arteries produced by platelets during aggregation, Ellis et al. *Science* 193, 1135–1137, 1976.

Several inhibitors of thromboxane synthesis are known including imidazole, Needleman et al. *Proc. Natl. Sci.* 74, pp. 1716–1720, 1977, and its derivatives such as UK-37, 248-01. Tyler et al., *Lancet* (1) pp. 629–632, 1981 and pyridine, Taniguchi et al. Abstract p. 82, Int. Prostaglandin Conference Washington D. C., May 27–31, 1979, and derivatives such as nicotine, Tai et al. Abstract p. 115 Fourth Int. Prostaglandin Conference Washington D. C. May 27–31 1979. These compounds divert the conversion of prostaglandin endoperoxides from TxA$_2$ into the classical prostaglandins PGD$_2$, PGE$_2$, PGF$_2$α and may be useful in preventing thrombosis by preventing vasoconstriction attributable to TxA$_2$. Oral administration of UK-37, 248-01 to man produced no consistent effect on blood pressure or heart rate or other side-effects or signs of toxicity. However experience with these compounds is limited, and it is probable that the full extent of the side effects caused thereby is not yet known.

Although there are materials known to have blood platelet antiaggregation properties, e.g. aspirin, prostaglandins and "CAMP inhibitors", they normally have some disadvantages, i.e. side-effects, limited effectiveness. In in vitro tests, the applicant has found that the administration of a thromboxane synthetase inhibitor in combination with a "CAMP inhibitor" produces a surprising degree of inhibition of platelet aggreation.

SUMMARY OF THE INVENTION

The present invention provides a novel method of inhibiting blood platelet aggregation comprising the use of a "CAMP inhibitor" together with an inhibitor of thromboxane synthetase. While inhibitors of thromboxane synthetase are only weak inhibitors of platelet aggregation, the addition of a small amount of a CAMP inhibitor has been found to result in a synergistic inhibition of platelet aggregation. It is not fully understood why the use of these inhibitors in combination produces a marked increase over the otherwise expected cumulative effects of these inhibitors to inhibit platelet aggregation. Nonetheless, such marked increases have been demonstrated using combinations of various thromboxane synthetase inhibitors and various "CAMP inhibitors".

In accordance with the preferred embodiment of the present invention, blood platelet aggregation is inhibited through the administration, either orally or parenterally, to a patient disposed toward undesirable platelet aggregation, of comparatively low doses of a cyclic AMP phosphodiesterase inhibitor in combination with a thromboxane synthetase inhibitor, to thereby produce a surprising degree of inhibition of platelet aggregation. In accordance with the present invention, the thromboxane synthetase inhibitor may be imidazole (including its derivatives) or pyridine (including its derivatives). Cyclic AMP phosphodiesterase inhibitors for use in accordance with the present invention include derivatives of quinazolinone and papaverine. It is also anticipated that dipyridamole (sold by BoehringerIngelheim under the trade name "persantin") and its derivatives, and as well as xanthine derivatives, may be suitable CAMP inhibitors for use in performing the methods of the present invention.

OBJECTS OF THE INVENTION

Accordingly, a primary object of the present invention is a provision of a method capable of producing a preselected degree of inhibition of platelet aggregation while minimizing the likelihood of experiencing deleterious side effects through the combined application of a cyclic AMP phosodiesterase inhibitor and a thromboxane synthetase inhibitor.

This and other objects of the present invention will become apparent from the following, more detailed description.

BRIEF DESCRIPTION OF THE DRAWINGS

FIG. 2a shows the results of blood platelets aggregated with collagen as a control; FIG. 2b records a test of a similar sample pretreated with an imidazole derivative prior to collagen addition; FIG. 2c records a test of a similar sample pretreated with a quinazolinone derivative prior to collagen addition; FIG. 2d records a similar test wherein the imidazole and quinazolinone derivatives of FIGS. 2b and 2c were both added to a similar sample prior to collagen addition, and wherein little or no aggregation was found to result.

DETAILED DESCRIPTION OF THE INVENTION

Figure 1:
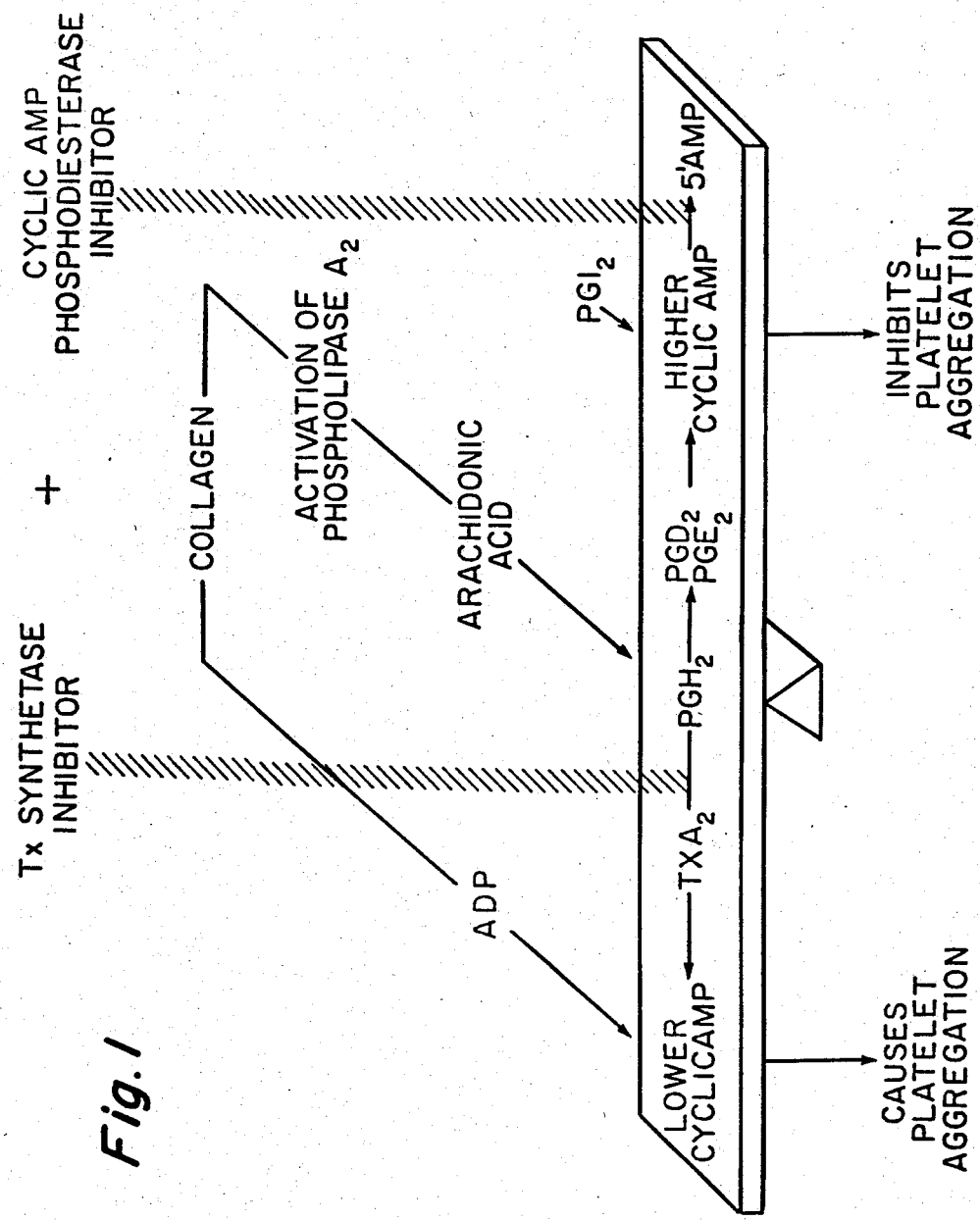
In FIG. 1 various biochemical pathways are illustrated which suggest some of the reactions which may be involved and/or effected by the simultaneous administration of a thromboxane synthetase inhibitor with a cyclic AMP phosphodiesterase inhibitor.

As used herein, the term "platelet-rich plasma" (PRP) refers to the supernatant plasma obtained after slow centrifugation of human blood. It contains large numbers of blood platelets but few red or white cells.

Also used herein, the term "collagen" refers to an acid solubilized extract of tendon (0.5 mg per ml protein) which is used to induce platelet aggregation.

In this testing, PRP was exposed to collagen, collagen and a "CAMP inhibitor" (such as a quinazolinone derivative (Anagrelide, BL-4162A from Bristol Laboratories) or papaverine), collagen and a thromboxane synthetase inhibitor (such as imidazole derivative (UK-37, 248-01 from Pfizer)), and collagen in combination with both a thromboxane sythetase inhibitor and a cyclic AMP phosphodiesterase inhibitor. The drugs were dissolved in ethanol or physiological saline solution.

For oral use, the drugs employed herein can be combined with conventional compatible organic or inorganic pharmaceutical carrier materials known to the art. Such materials include, for example, water, gelatin, gums, lactose, starches, magnesium stearate, talc, vegetable oils, polyalkylene glycols and the like. Such pharmaceutical preparations may be in unit dosage form and may additionally contain other therapeutically valuable substances or conventional adjuvants such as preservatives, stabilizing agents, wetting agents, emulsifying agents, buffers and the like. The pharmaceutical preparations can be in conventional solid dosage forms such as tablets, capsules, dragees and the like, conventional liquid forms such as solutions, suspensions, emulsions and the like and other conventional dosage forms such as dry ampules, suppositories and the like. Such preparations may be submitted to conventional pharmaceutical expedients such as, for example, sterilization and the like.

One of the primary objects of the present invention is to reduce the dosage to the subject of compounds by comparison to the amounts which would be required to produce a corresponding inhibition of blood platelet aggregation in a given individual were only a single compound administered to that individual for that purpose. By lowering the dosages required to achieve the desired antiaggregating effect in an individual, it is anticipated that the undesirable side-effects expected from higher dosages of such drugs may be avoided. Accordingly, in selecting dosages of a thromboxane synthetase inhibitor and "cyclic AMP inhibitor" it is, in every event, anticipated that such drugs should be applied in combination in dosages which are lower than those which would be necessary to produce a corresponding inhibition if such compounds were applied either alone, or if such dosages where determined soley on the basis of the separate antiagregating effects heretofore known or suggested for such compounds. In view of the information and examples disclosed hereinafter, those of ordinary skill in the art will have little difficulty in determining appropriate combined dosages of thromboxane synthetase and cyclic AMP inhibitors. The following non-limiting examples illustrate some of the possible dosage combinations. Anagrelide at 5 mg/kg body weight in combination with UK37, 248-01 at 1 mg/kg body weight. Papaverine at 2 mg/kg body weight in combination with imidazole at 10 mg/kg body weight. Dipyridamole at 1 mg/kg body weight in combination with UK-37, 248-01 at 2 mg/kg body weight.

For parenteral use, drug combinations employed herein can be administered in conventional pharmaceutical forms, preferably parenteral forms, for example, solutions, suspensions and emulsions. Examples of conventional pharmaceutical carrier materials which may be utilized in such forms include, water for injection, vegetable oils, polyalkylene glycols and the like. Such preparations can be subjected to conventional pharmaceutical expedients such as sterilization and can contain pharmaceutical adjuvants such as preservatives, stabilizing agents, wetting agents, emulsifying agents, salts for the adjustments of osmotic pressure, buffers and the like.

The composition of this invention can be administered to mammals disposed toward undesired (excessive) blood platelet aggregation. Individuals can be disposed to hyperthrombotic complications due to surgery, late pregnancy, phlebitis, atherosclerosis, recent stroke, recent myocardial infarction and the like. It is also contemplated that the process of this invention can be employed as long term prophylactic treatment of persons disposed to excessive platelet aggregation. The oral route of administration is preferred for chronic and prophylactic use. Parenteral use is indicated for those excessively prone to acute thromboembolic episodes, and when immediate onset of activity is desired. In each specific instances, the attending diagnostician will determine the exact dosage, amount and frequency taking into account related health factors of the subject.

EXAMPLE 1

In order to measure the blood platelet aggregating response to collagen, the following procedure was employed.

Human blood was collected into 0.1 volume of 3.8% trisodium citrate and centrifuged at 250 g for 15 minutes at 20°–22° C. to prepare an upper layer of platelet rich plasma (PRP). Aggregation of the platelets was studied photometrically in siliconized tubes at 37° C. with the continuous regarding of light transmission (Aggregometer, Chronolog Corp. Broomall, Pa.). Each experiment was conducted by comparing the light transmission of a control (PRP with added vehicle) with the light transmission of a sample of PRP (0.5 ml) with added aggregating agent and/or inhibitors. Aggregation was allowed to go on for 2.5 minutes. The "extent of aggregation" refers to the maximal increase of light transmission found after the addition of the agent expressed in arbitrary units.

| Collagen (microliter) | Time of Aggregation (Min.) | Extent of Aggregation |
| --- | --- | --- |
| 5 | 1 | 11 |
| 5 | 1.5 | 38 |
| 5 | 2 | 47 |
| 5 | 2.5 | 52 |

Figure 2A:
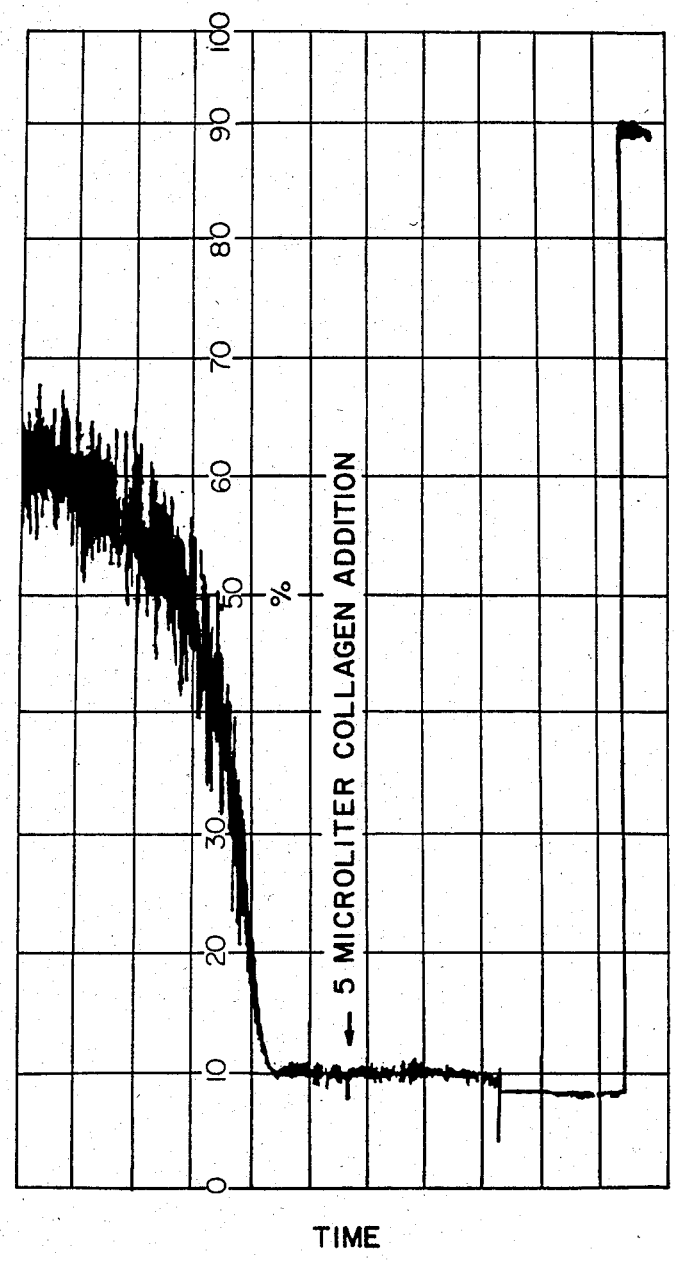
FIGS. 2a–d are representative light transmission traces of human blood platelet samples wherein increasing X-axis values represent the passage of time and increasing Y-axis values indicate greater degree of platelet aggregation.
Figure 2B:
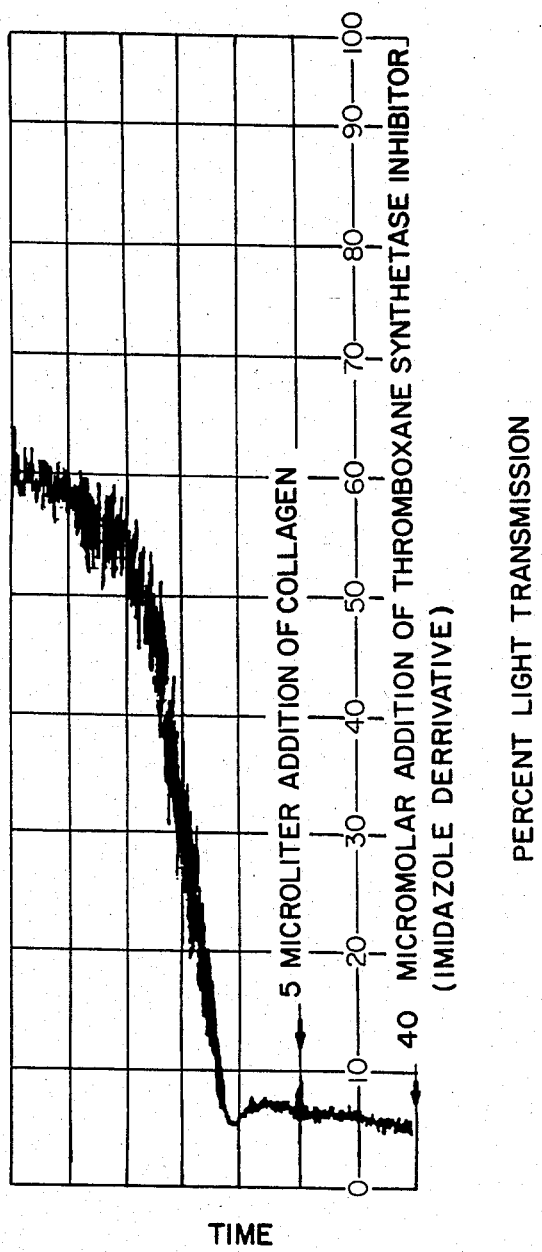
Figure 2C:
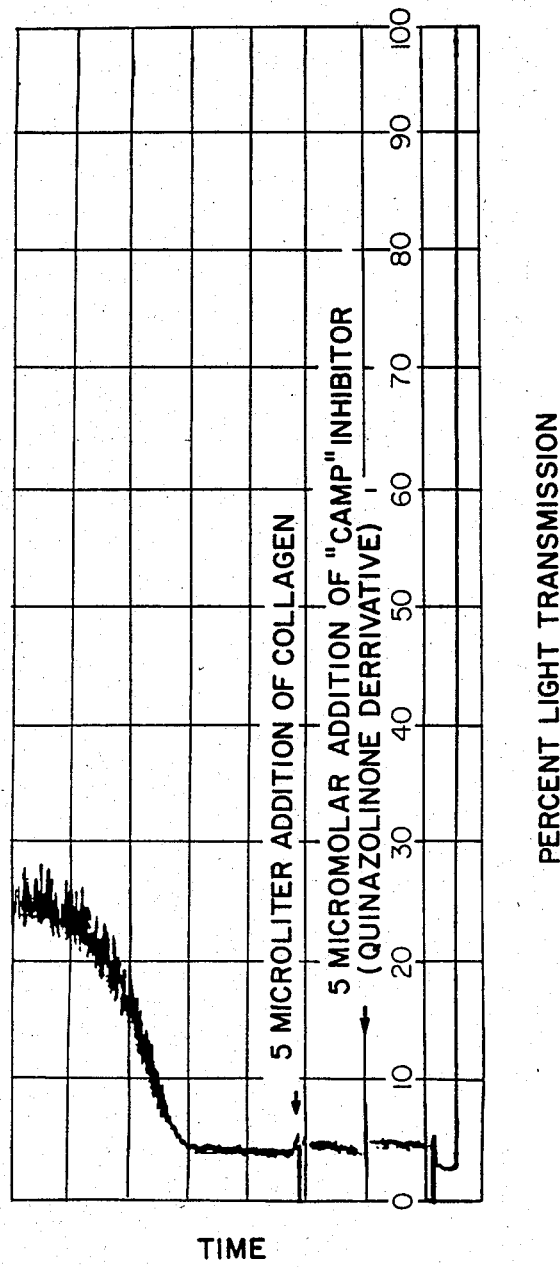
Figure 2D:
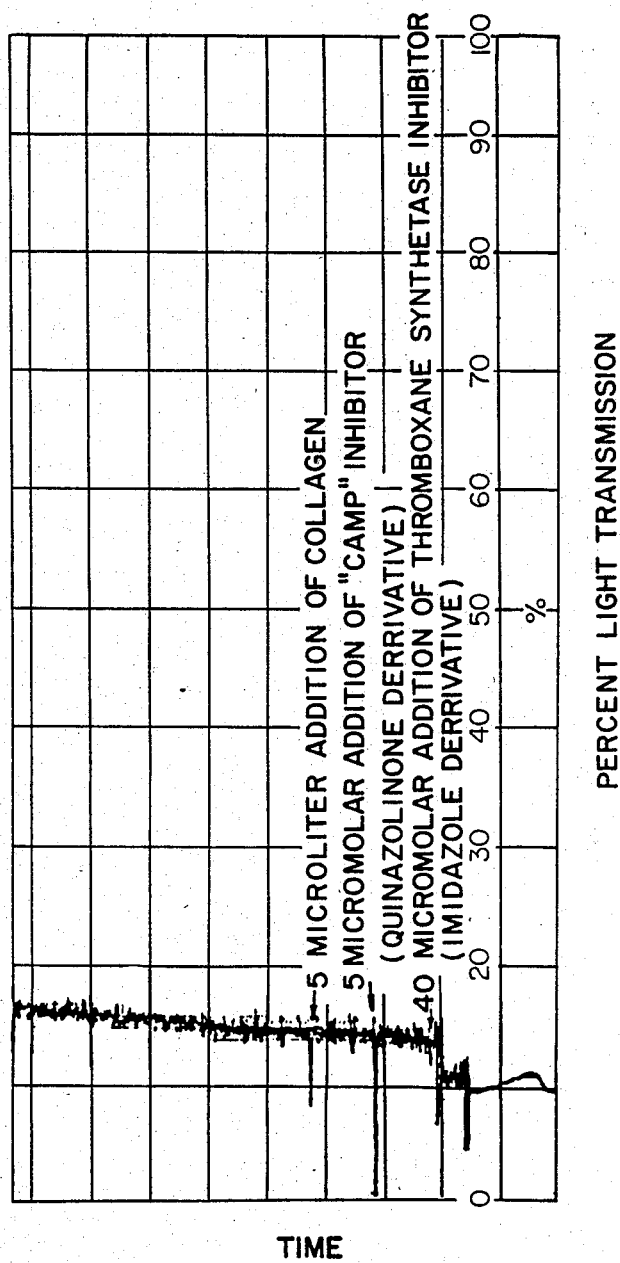

A representative light transmission trace of such an aggregation appears as FIG. 2a.

EXAMPLE 2

In accordance with the procedure of Example 1, the following example illustrates the surprising augmentation that Anagrelide produces to the inhibitory effect of UK-37, 248-01 on platelet aggregation.

| | 1st Addition (1 min before) | 2nd Addition (0.5 min before) | Collagen | Extent of Aggregation |
| --- | --- | --- | --- | --- |
| 1. | — | — | 10 µl | 61 |
| 2. | — | Anagrelide (1 µM) | 10 µl | 57 |
| 3. | UK-37,248-01 (2 µM) | Anagrelide (1 µM) | 10 µl | 55 |
| 4. | UK-37,248-01 (4 µM) | Anagrelide (1 µM) | 10 µl | 49 |
| 5. | UK-37,248-01 (10 µM) | Anagrelide (1 µM) | 10 µl | 35 |
| 6. | UK-37,248-01 (20 µM) | Anagrelide (1 µM) | 10 µl | 22 |
| 7. | UK-37,248-01 (100 µM) | Anagrelide (1 µM) | 10 µl | 20 |
| 8. | UK-37,248-01 (500 µM) | Anagrelide (1 µM) | 10 µl | 9 |
| 9. | UK-37,248-01 (100 µM) | — | 10 µl | 57 |
| 10. | UK-37,248-01 (500 µM) | — | 10 µl | 53 |

It may be seen that very little reduction in platelet aggregation resulted from the administration of UK-37,248-01 alone (test 9 and 10) or anagrelide alone (test 2). However, the combined use of UK-37,248-01 with anagrelide produces a greater inhibition of aggregation than can be explained by simple additive effects (e.g. test 7). UK-37,248-01 is 1-(2-4-carboxyphenoxyethyl-)imidazole. Anagrelide, BL-4162A, is the dichloro-analogue of 6-methyl-1,2,3,5 tetrahydroimadazo[2,1-b]-quinazolin-2-one.

EXAMPLE 3

This example using PRP obtained from a different donor, illustrates the combination of Anagrelide with UK-37,248-01 is clearly superior to either drug along at several concentrations of collagen.

| 1st Addition (1 min before) | 2nd Addition (0.5 min before) | Collagen | Extent of Aggregation |
| --- | --- | --- | --- |
| — | — | 2 µl | 49 |
| — | — | 5 µl | 54 |
| UK-37,248-01 (40 µM) | Anagrelide (10 µM) | 2 µl | 0 |
| UK-37,2481 (40 µM) | Anagrelide (10 µM) | 5 µl | 3 |
| UK-37,2481 (40 µM) | Anagrelide (10 µM) | 10 µl | 17 |
| UK-37,248-01 (40 µM) | Anagrelide (10 µM) | 20 µl | 24 |
| UK-37,248-01 (40 µM) | Anagrelide (10 µM) | 50 µl | 39 |
| — | Anagrelide (10 µM) | 2 µl | 8 |
| — | Anagrelide (10 µM) | 5 µl | 25 |
| — | Anagrelide (10 µM) | 10 µl | 45 |
| UK-37,248-01 (200 µM) | — | 5 µl | 53 |

EXAMPLE 4

This example, using PRP obtained from a different donor, illustrates that the effectiveness of UK-37,248-01 is markedly increased by a class of "CAMP inhibitor" other than the quinazolinone, Anagrelide, using the pyrimidopyrimidine derivative RA233.

| 1st Addition (1 min before) | 2nd Addition (0.5 min before) | Collagen | Extent of Aggregation |
|---|---|---|---|
| — | — | 5 μl | 45 |
| UK-37,248-01 (20 μM) | — | 5 μl | 38 |
| — | RA233 (10 μM) | 5 μl | 31 |
| UK-37,248-01 (20 μM) | RA233 (10 μM) | 5 μl | 1 |

EXAMPLE 5

This example, using PRP obtained from yet another donor, illustrates that the effectiveness of several different thromboxane synthesis inhibitors (UK-37,248-01, imidazole, methyl imidazole and nicotine) are enhanced by different "CAMP phosphodiesterase inhibitors" including Anagrelide, papaverine and isobutyl methylxanthine. (IBMX).

| 1st Addition (1 min before) | 2nd Addition (0.5 min before) | Collagen | Extent of Aggregation |
|---|---|---|---|
| — | — | 5 μl | 58 |
| UK-37,248-01 (40 μM) | Anagrelide (5 μM) | 5 μl | 10 |
| UK-37,248-01 (40 μM) | — | 5 μl | 55 |
| — | Anagrelide (5 μM) | 5 μl | 47 |
| Imidazole (40 mM) | Anagrelide (5 μM) | 5 μl | 7 |
| Imidazole (40 mM) | — | 5 μl | 52 |
| Methyl-imidazole (2.5 mM) | Anagrelide (5 μM) | 5 μl | 6 |
| Methyl-imidazole (2.5 mM) | — | 5 μl | 55 |
| Nicotine (2.5 mM) | Anagrelide (5 μM) | 5 μl | 8 |
| Nicotine (2.5 mM) | — | 5 μl | 47 |
| — | Papaverine (120 μM) | 5 μl | 52 |
| Nicotine (2.5 mM) | Papaverine (120 μM) | 5 μl | 5 |
| Imidazole (40 mM) | Papaverine (120 μM) | 5 μl | 10 |
| Methyl-imidazole (2.5 mM) | Papaverine (120 μM) | 5 μl | 13 |
| — | IBMX (100 μM) | 5 μl | 36 |
| Imidazole (40 mM) | IBMX. (100 μM) | 5 μl | 15 |

EXAMPLE 6

This example illustrates another experiment performed to verify that UK-37,248-01 (UK) causes inhibited thromboxane synthesis and increases formation of other prostaglandins. At the end of aggregation induced by collagen, samples of PRP were taken from the analysis of thromboxane $B_2$ ($TxB_2$) and $PGE_2$ by radioimmunoassay.

| 1st Addition | 2nd Addition | Collegen | Extent of Aggn. | $T \times B_2$ (P mol/ml) | $PGE_2$ (P mol/ml) |
|---|---|---|---|---|---|
| — | — | — | 0 | <5 | <5 |
| — | — | 5 μl | 52 | 280 | 20 |
| UK.(40 μM) | — | 5 μl | 53 | 6.6 | 370 |
| — | Anagrelide (1 μM) | 5 μl | 50 | 170 | 14 |
| — | Anagrelide (2.5 μM) | 5 μl | 37 | 130 | 27 |
| UK.(40 μM) | Anagrelide (1 μM) | 5 μl | 28 | 8.2 | 175 |
| UK. (40 μM) | Anagrelide (2.5 μM) | 5 μl | 6 | <5 | 260 |

From this example it can be seen that large amounts of $PGE_2$ are formed only in the presence UK-37,248-01.

FIG. 1 is a diagrammatic representation of various biochemical pathways which may suggest some of the reactions involved and/or effected by the simultaneous administration of thromboxane synthetase inhibitor with a cyclic AMP phosphodiesterase inhibitor. If the theory suggested in FIG. 1 is correct, it would indicate that the herein disclosed profound synegerism may occur only when platelets are activated to produce prostaglandins by adhesion to collagen in the damaged vessel. However, the theoretical activities of the thromboxane synthetase inhibitor and cyclic AMP phosphodiesterase inhibitor set forth in FIG. 1 do not completely explain the synergestic results reported herein. Accordingly, it is not fully understood why the use of these inhibitors in combination produces such marked increased in inhibition of platelet aggregation.

In FIG. 2, representative light transmission traces similar to those obtained in the performance of examples 1-6 are provided. FIG. 2a is a light transmission trace of collagen induced aggregation over time similar to that reported in example 1 above. FIG. 2b is a similar light transmission trace similar to that obtained in tests 9 and 10 of example 2, but wherein a 40 micromolar solution of UK was added prior to a 5 microliter addition of collagen. FIG. 2c is a light transmission test similar to that obtained in performing test 2 of example 2, but at a higher concentration (5 micromolar) of quinazolinone derivative prior to a 5 microliter collagen addition. FIG. 2d is a light transmission trace similar to those obtained in performing tests 3-8 of example no. 2, but wherein the concentration of UK and quinazolinone are the same as used in obtaining the light transmission traces of FIGS. 2b and 2c. As seen in FIG. 2d the combined anti-aggregating effect of these imidazole and quinazolinone derivatives is marketly greater than would be expected from the combined effects of these agents when tested alone. The data represented in FIG. 2 is thus consistent with the data reported in examples 1-6 above.

As seen from the above, novel methods are provided for reducing the dosage of cyclic AMP phosphodieterase inhibitor or thromboxane synthetase inhibitor needed to achieve a desired degree of platelet aggregation inhibition. Such cyclic AMP phosphodiesterase inhibitors include, for example, dipyridamole and its derivatives, particularly 2,6-bis-(diethanolamino)-4-piperidino-pyrimido-[5,4d]-pyrimidine (compound RA233) and 2,4,6-trimorpholinopyrimido-[5,4d]-pyrimidine. Such thromboxane synthetase inhibitors include, pyridine and imidazole derivatives. For example, pyridine derivatives substituted at the $\beta$ or $\alpha$ position of the pyridine ring, such as $\beta$-[4-(2-carboxy-1- propenyl)benzyl]pyridine hydrochloride (OKY-1555), hexyl nicotinate or nicotine are preferred, while preferred imidazole derivatives include derivatives substituted in the α position such as 1-carboxyhexyl-, 1-carboxyheptyl, and 1-carboxyoctyl-imidazoles. By administering such inhibitors in combinations effective to achieve the desired degree of inhibition, yet at lower dosages than otherwise required, the likelihood of causing undesirable side effects is substantially reduced.

We claim:

1. A method for inhibiting blood platelet aggregation comprising administering to an individual disposed toward undesirable blood platelet aggregation a combination of amounts of a thromboxane synthetase inhibitor and an inhibitor of cyclic AMP phosphodiesterase which together are effective to inhibit blood platelet aggregation in said individual, said thromboxane synthetase inhibitor when tested alone in vitro producing a degree of blood platelet aggregation inhibition which is a minor proportion of the degree achieved by said combination.

2. A method according to claim 1 wherein the mode of administration is oral.

3. A method according to claim 1 wherein the mode of administration is parenteral.

4. A method for inhibiting platelet aggregation in accordance with claim 1 wherein said thromboxane synthetase inhibitor is imidazole.

5. The method of claim 1 wherein said thromboxane synthetase inhibitor is an imidazole derivative.

6. The method of claim 1 wherein said thromboxane synthetase inhibitor is pyridine.

7. The method of claim 1 wherein said thromboxane synthetase inhibitor is a pyridine derivative.

8. The method of claim 1 wherein said inhibitor cyclic AMP phosphodiesterase is quinazolinone.

9. The method of claim 1 wherein said inhibitor of cyclic AMP phosphodiesterase is a quinazolinone derivative.

10. The method of claim 1 wherein said inhibitor of cyclic AMP phosphodiesterase is a pyrimido-pyrimidine derivative.

11. The method of claim 1 wherein said inhibitor of cycli AMP phosphodiesterase is papaverine.

12. The method of claim 1 wherein said inhibitor of cyclic AMP phosphodiesterase is a methyl xanthine.

13. The method of claim 1 wherein the combined amounts of said inhibitors are administered to achieve a preselected degree of aggregation inhibition and are less than the combined amounts of said inhibitors which would be predicted as necessary to achieve said degree of inhibition based upon their individual activities.

14. A method of reducing the dosage of a thromboxane synthetase inhibitor needed to achieve a desired degree of platelet aggregation inhibition in an individual, comprising the step of administering a lowered dose of said inhibitor in combination with an amount of cyclic AMP phosphodiesterase inhibitor which is effective in combination with said thromboxane synthetase inhibitor to achieve said desired degree of inhibition, said thromboxane synthetase inhibitor when tested alone in vitro producing a degree of blood platelet aggregation inhibition which is a minor proportion of the degree achieved by said combination, whereby the likelihood of causing undesirable side effects in said individual is said substantially reduced.

15. A method of reducing the dosage of a cyclic AMP phosphodiesterase inhibitor needed to achieve a desired degree of platelet aggregation inhibition in an individual, comprising the step of administering a lowered dose of said cyclic AMP phosphodiesterase inhibitor in combination with an amount of a thromboxane synthetase inhibitor which is effective in combination with said cyclic AMP phosphodiesterase inhibitor to achieve said desired degree of inhibition, said thromboxane synthetase inhibitor when tested alone in vitro producing a degree of blood platelet aggregation inhibition which is a minor proportion of the degree achieved by said combination, whereby the likelihood of causing undesirable side effects in said individual is substantially reduced.

* * * * *